(12) United States Patent
Kang

(10) Patent No.: US 9,568,398 B2
(45) Date of Patent: Feb. 14, 2017

(54) TEST APPARATUS OF FLUIDIC SAMPLE AND CONTROL METHOD THEREOF

(71) Applicant: SAMSUNG ELECTRONICS CO., LTD., Suwon-si (KR)

(72) Inventor: Hyun Suk Kang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 104 days.

(21) Appl. No.: 14/093,897

(22) Filed: Dec. 2, 2013

(65) Prior Publication Data
US 2015/0143924 A1  May 28, 2015

(30) Foreign Application Priority Data

Nov. 22, 2013  (KR) .................. 10-2013-0142787

(51) Int. Cl.
| G01L 1/00 | (2006.01) |
|---|---|
| G01L 5/00 | (2006.01) |
| G01N 1/00 | (2006.01) |
| G01N 35/00 | (2006.01) |
| G01N 35/04 | (2006.01) |
| G01N 33/49 | (2006.01) |

(52) U.S. Cl.
CPC .......... *G01N 1/00* (2013.01); *G01N 35/00029* (2013.01); *G01N 33/49* (2013.01); *G01N 2035/0491* (2013.01)

(58) Field of Classification Search
CPC .................. G01N 33/492; G01N 2035/00148; G01N 2035/00089; G01N 1/28; G01N 21/35; G01N 29/02; G01N 30/28; G01N 33/48785; G01N 35/00613; G01N 35/1011; G01N 35/1095; G01N 9/04
USPC .................. 73/862.381, 863, 864.91, 864.83
See application file for complete search history.

(56) References Cited

U.S. PATENT DOCUMENTS

| 6,086,767 A * | 7/2000 | Walters .............. B01D 11/0203 210/198.2 |
|---|---|---|
| 2010/0094172 A1* | 4/2010 | List .................... A61B 5/15146 600/583 |
| 2011/0195490 A1* | 8/2011 | Kang .................. G01N 33/492 435/287.1 |

\* cited by examiner

*Primary Examiner* — Harshad R Patel
*Assistant Examiner* — Brandi Hopkins
(74) *Attorney, Agent, or Firm* — Sughrue Mion, PLLC

(57) ABSTRACT

Disclosed herein are a test apparatus of a fluidic sample, which tests the fluidic sample, and a control method thereof. The test apparatus of the fluidic sample includes a housing, an installing member in which a cartridge receiving a fluid is inserted, a pressing member which is disposed in the housing to press the cartridge and perform an inspection of the fluid, a driving unit of which at least a part is coupled to the pressing member so as to movably drive the pressing member, and a sensing unit of which at least a part is opposite to the driving unit so as to sense a position of the driving unit. According to the present invention, since the sensing unit can recognize the position of the driving unit, the pressing member can apply uniform pressure to the cartridge.

23 Claims, 14 Drawing Sheets

TEST APPARATUS OF FLUIDIC SAMPLE AND CONTROL METHOD THEREOF

CROSS-REFERENCE TO RELATED APPLICATION

This application claims the benefit of Korean Patent Application No. 2013-0142787, filed on Nov. 22, 2013 in the Korean Intellectual Property Office, the disclosure of which is incorporated herein by reference.

BACKGROUND

1. Field

Embodiments of the present invention relate to a test apparatus of a fluidic sample, which tests the fluidic sample, and a control method thereof.

2. Description of the Related Art

A test apparatus of a fluidic sample and a control method thereof are used in various fields such as environment monitoring, food inspection, and medical diagnosis. Formerly, in order to perform a test according to predetermined protocols, skilled experimenters should manually carry out various processes such as multiple reagent injections, mixing, isolating and transferring, reaction, and centrifugation, and these processes cause errors in inspection results.

In order to solve the problem, there has been developed a compact and automated apparatus which can rapidly analyze a test material.

A characteristic reaction of a test material and a specific material may be used in order to detect the test material contained in a fluidic sample. And optical data is measured by using an optical sensor, and then a concentration of the test material is obtained from a measured optical data size or a change amount thereof.

In the inspection of a fluidic sample, a cartridge receiving the fluidic sample is pressed by a pressing member, and the fluidic sample is transferred and inspected. At this time, the pressure applied to the cartridge may be changed time after time. When the applied pressure is excessive, the fluidic sample or a reagent for the inspection may leak to the outside of the cartridge. When the applied pressure is insufficient, the fluidic sample may not be transferred to an inspecting part in which the reagent is received.

SUMMARY

Therefore, it is an aspect of the present invention to provide a test apparatus of a fluidic sample, which can sense a position of a driving unit so that a consistent pressure is always applied to a cartridge, and a control method thereof.

Additional aspects of the invention will be set forth in part in the description which follows and, in part, will be obvious from the description, or may be learned by practice of the invention.

In accordance with one aspect of the present invention, a test apparatus of a fluidic sample includes a housing, an installing member in which a cartridge receiving a fluid is inserted, a pressing member which is disposed in the housing to press the cartridge and perform an inspection of the fluid, a driving unit of which at least a part is coupled to the pressing member so as to movably drive the pressing member; and a sensing unit of which at least a part is opposite to the driving unit so as to sense a position of the driving unit.

A protrusion may be extended from one side of the driving unit so that the sensing unit senses the position of the driving unit.

The sensing unit may be a proximity sensor which senses the position of the driving unit by sensing whether the protrusion comes close to the sensing unit.

The proximity sensor may be an optical sensor comprising a light emitting part emitting light and a light receiving part receiving the light emitted from the light emitting part, and the optical sensor may sense the position of the driving unit by sensing whether the protrusion is located between the light emitting part and the light receiving part.

The sensing unit may be a weight sensor which senses the position of the driving unit according to whether the protrusion is in contact with the sensing unit.

The driving unit may include a motor providing power to move the pressing member, and a lever transmitting the power of the motor to the pressing member; and the protrusion may be extended from the lever toward the sensing unit.

The sensing unit may be located at a lower side of the lever.

The pressing member may include a head portion coupled with the driving unit, and a body portion pressing the cartridge.

A contacting surface of the body portion, which is in contact with the cartridge, may include an inclined portion which is at least partially inclined on the contacting surface.

The inclined portion may be provided to be upwardly inclined toward an outside of the body portion.

A contacting surface of the body portion, which is in contact with the cartridge, may include at least one protruding portion which at least partially protrudes from the contacting surface.

A contacting surface of the body portion, which is in contact with the cartridge, may include at least one concave portion which is at least partially concave in the contacting surface.

The test apparatus may further include a frame of which one side is coupled with the driving unit, and the other side is coupled with the installing member.

The test apparatus may further include a control part which senses a movement degree of the driving unit and controls the driving unit to uniformly move the pressing member.

In accordance with another aspect of the present invention, a test apparatus of a fluidic sample includes a housing, a frame which is disposed in the housing, a pressing member coupled to one side of the frame and moving between a first position which presses a cartridge receiving a fluid and performs an inspection of the fluid and a second position which is spaced apart from the cartridge, a driving unit which is coupled to the other side of the frame so as to move the pressing member between the first and second positions, and a sensing unit which recognizes movement of the driving unit and determines whether the pressing member is located at the first position or the second position.

The sensing unit may be a proximity sensor which senses the position of the driving unit by sensing whether at least a part of the driving unit comes close to the sensing unit.

The sensing unit may be a weight sensor which senses the position of the driving unit according to whether at least a part of the driving unit is in contact with the sensing unit.

The driving unit may include a motor providing power to move the pressing member, a lever transmitting the power of the motor to the pressing member, and a protrusion extended from the driving unit toward the sensing unit so as to be moved toward the sensing unit.

In accordance with yet another aspect of the present invention, a control method of a test apparatus of a fluidic sample including a pressing member which presses a cartridge receiving a fluid, a driving unit which movably drives the pressing member, and a sensing unit which senses a position of the driving unit includes moving at least a part of the driving unit, and recognizing a position of the driving unit by the sensing unit, and installing the cartridge, and moving the driving unit to press the cartridge.

The recognizing of a position of the driving unit may recognize a starting point of the driving unit.

The control method may further include moving the driving unit to the recognized starting point after an analysis of the fluid in the cartridge is performed.

The test apparatus of the fluidic sample may further include a control part which controls a movement degree of the driving unit, and the control part may recognize a position of the driving unit sensed by the sensing unit as a starting point of the driving unit, may sense the movement degree of the driving unit, and may control the pressing member to apply uniform pressure to the cartridge.

The control part may perform an inspection when the driving unit is sensed by the sensing unit, and may move the driving unit to the starting point when the driving unit is not sensed by the sensing unit.

The recognizing of a position of the driving unit may recognize one point at which the driving unit moves the pressing member so as to press the cartridge.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Reference will now be made in detail to the embodiments of the present invention, examples of which are illustrated in the accompanying drawings.

Figure 1:
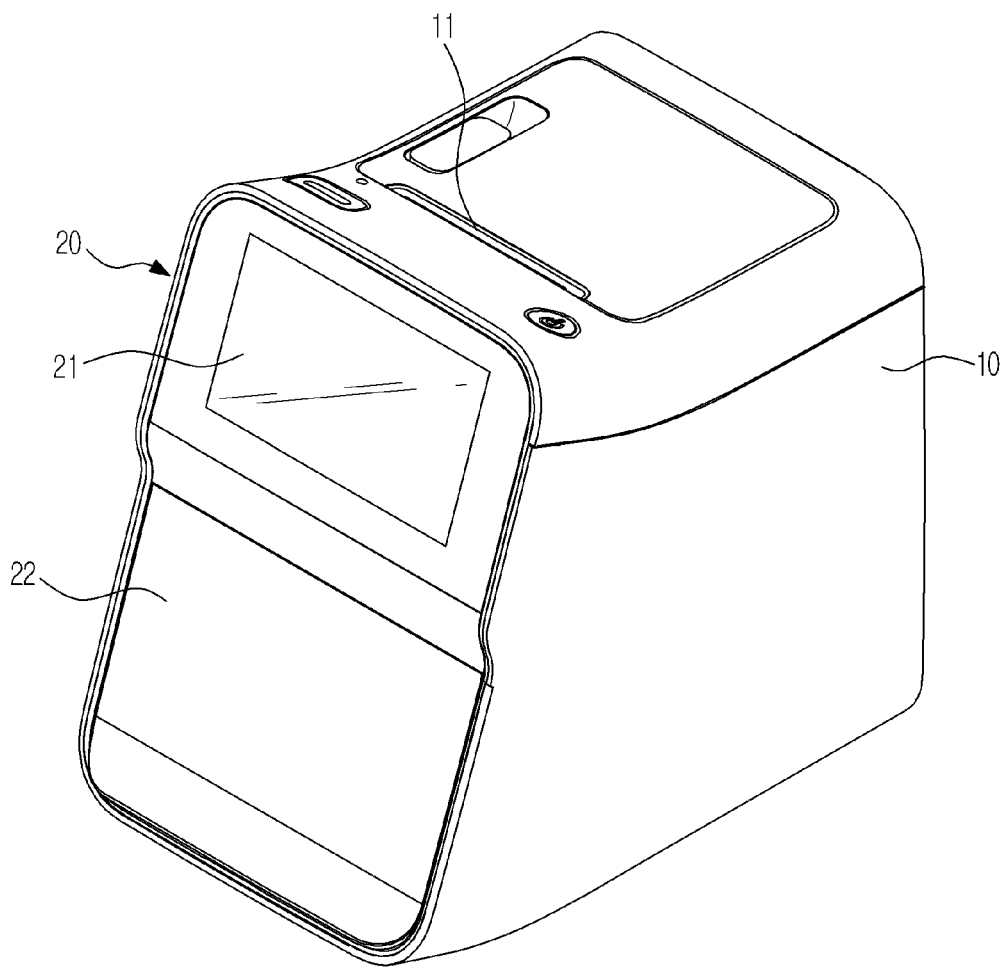
FIG. 1 is a view illustrating an external appearance of a test apparatus of a fluidic sample in accordance with one embodiment of the present invention.
Figure 2:
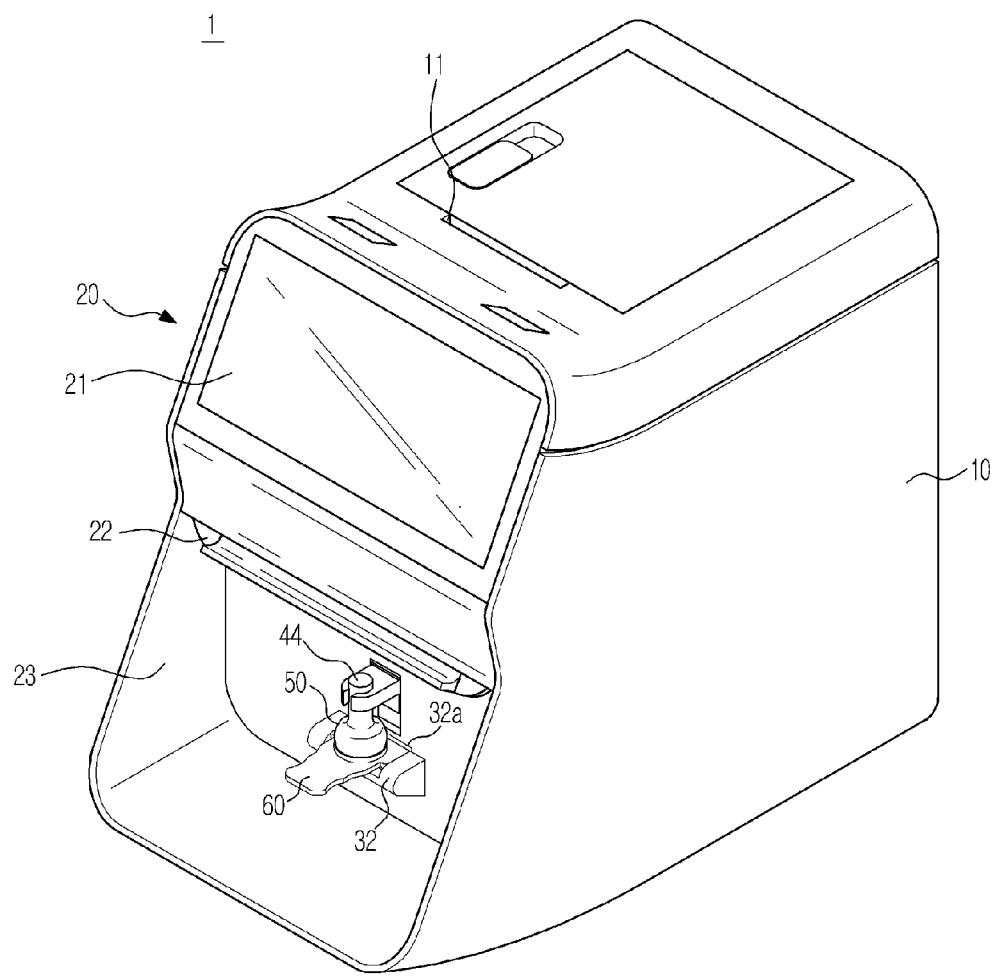
FIG. 2 is a view illustrating a state in which a door of a test apparatus of a fluidic sample is opened in accordance with one embodiment of the present invention.

FIG. 1 is a view illustrating an external appearance of a test apparatus of a fluidic sample in accordance with one embodiment of the present invention, and FIG. 2 is a view illustrating a state in which a door of a test apparatus of a fluidic sample is opened in accordance with one embodiment of the present invention.

As illustrated in FIGS. 1 and 2, a test apparatus 1 of a fluidic sample in accordance with one embodiment of the present invention includes a housing 10 defining an external appearance thereof, and a door module 20 disposed at a front side of the housing 10.

The door module 20 may include a display part 21, a door 22, and a door frame 23. The display part 21 and the door 22 may be disposed at a front side of the door frame 23. The display part 21 may be disposed at an upper side of the door 22. The door 22 may be slidably provided to be located at a rear side of the display part 21 when slid and opened.

The display part 21 displays information on sample analysis contents, sample analysis operation states, or the like. An installing member 32 in which a cartridge 60 receiving a fluidic sample is installed may be provided at the door frame 23. A user slides and opens the door 22 upwardly, installs the cartridge 60 in the installing member 32, slides and closes the door downwardly, and then performs an analysis operation.

Figure 5:
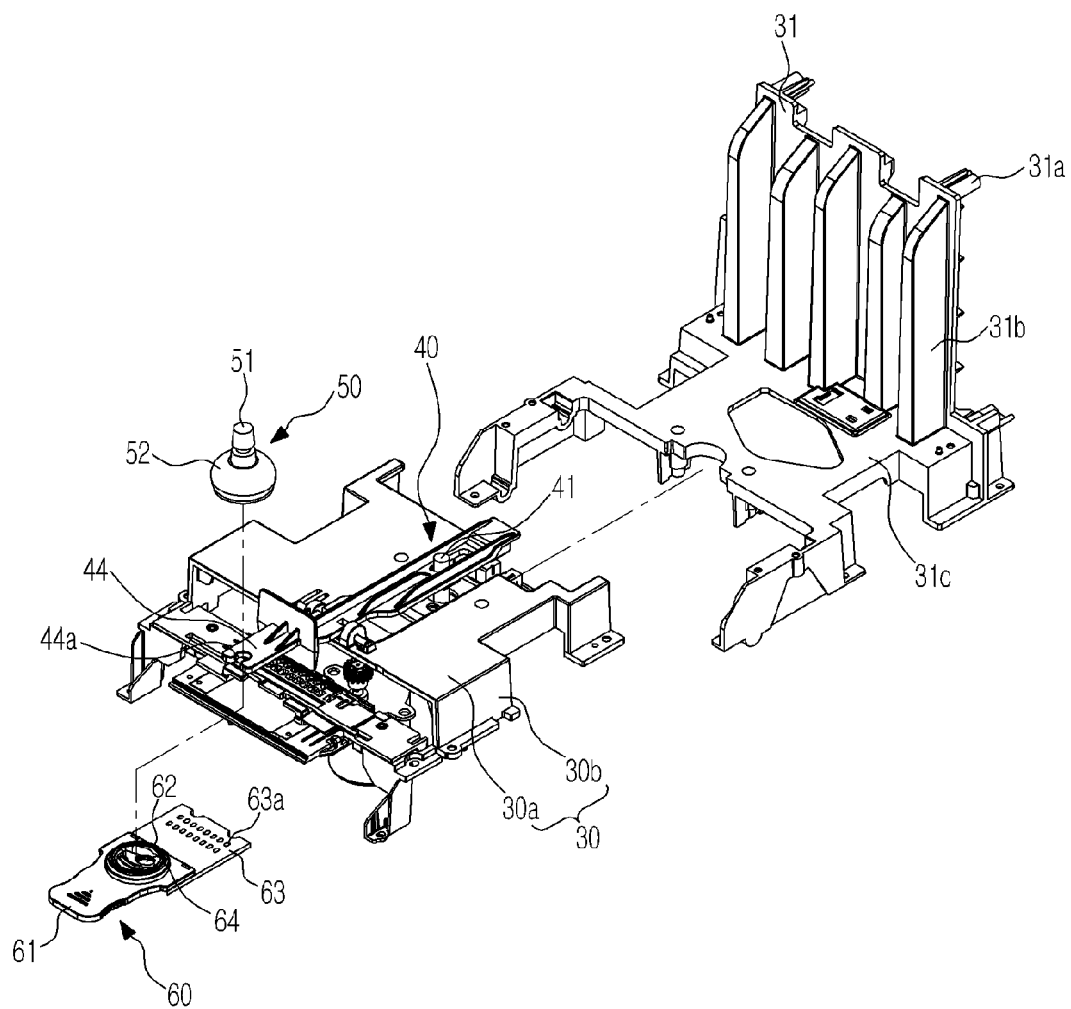
FIG. 5 is a view illustrating a state in which a part of construction elements is disassembled in a test apparatus of a fluidic sample in accordance with one embodiment of the present invention.

A fluidic sample is injected into the cartridge 60 and reacts with a reagent in an inspection part 63 (referring to FIG. 5). The cartridge 60 is inserted into the installing member 32 and then pressed by a pressing member 50 so that the fluidic sample in the cartridge 60 is introduced into the inspection part 63.

Also, besides the display part 21, an output part 11 may be further provided so as to output inspection results as a separate printed matter.

Figure 3:
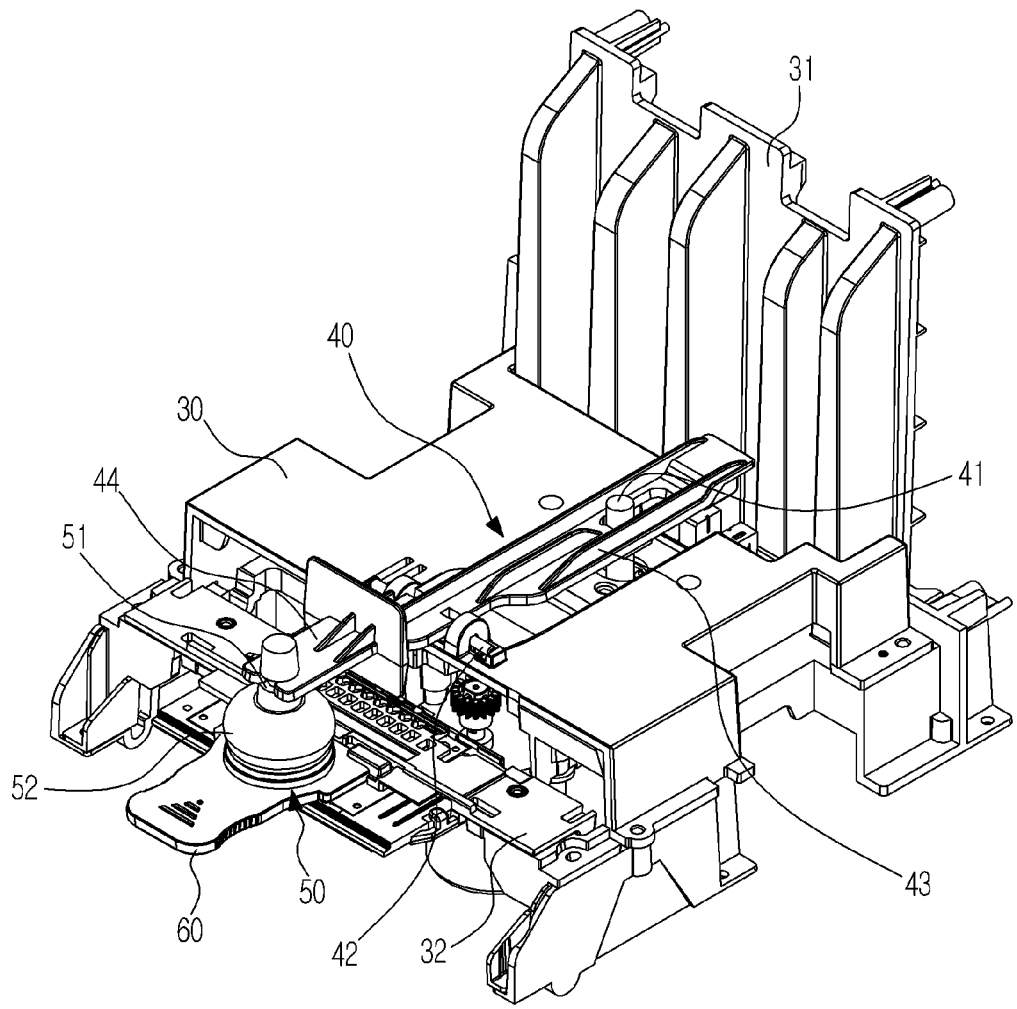
FIG. 3 is a view illustrating an inside of a test apparatus of a fluidic sample in accordance with one embodiment of the present invention.
Figure 4:
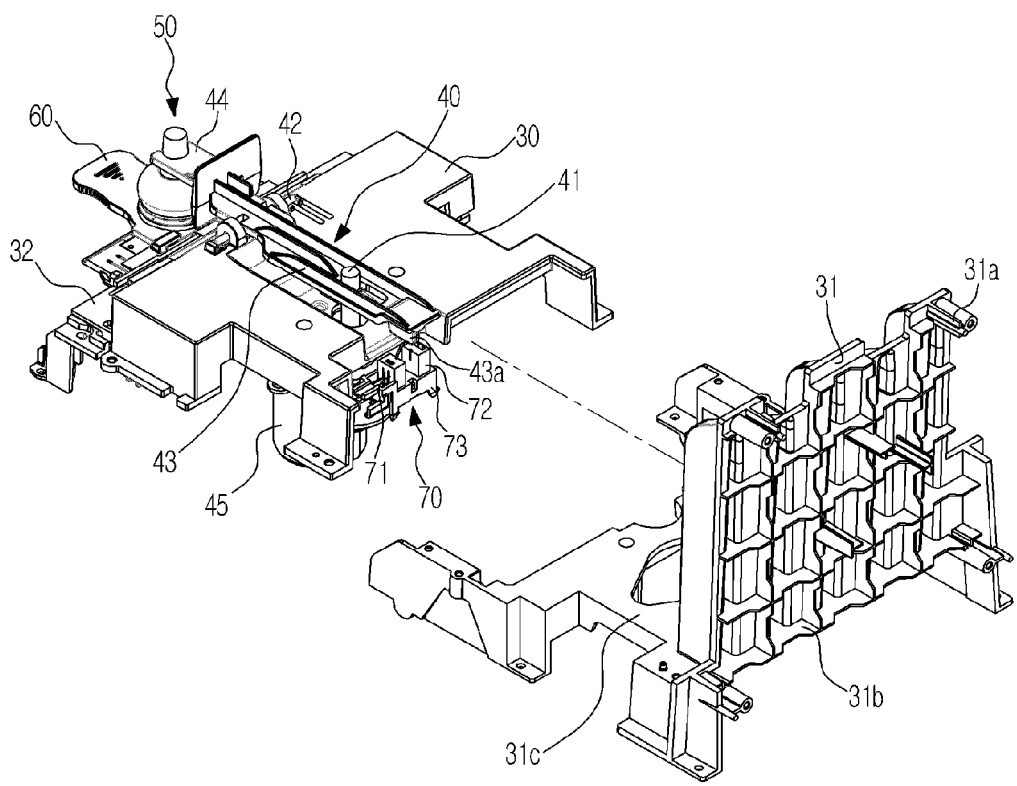
FIG. 4 is a view illustrating a state in which a rear panel is disassembled in a test apparatus of a fluidic sample in accordance with one embodiment of the present invention.

FIG. 3 is a view illustrating an inside of a test apparatus of a fluidic sample in accordance with one embodiment of the present invention, FIG. 4 is a view illustrating a state in which a rear panel is disassembled in a test apparatus of a fluidic sample in accordance with one embodiment of the present invention, and FIG. 5 is a view illustrating a state in which a part of construction elements is disassembled in a test apparatus of a fluidic sample in accordance with one embodiment of the present invention.

As illustrated in FIGS. 3 to 5, the test apparatus 1 of the fluidic sample includes the pressing member 50 pressing the cartridge 60, a driving unit 40 driving the pressing member 50 to be movable, and a sensing unit 70 sensing a position of the driving unit 40.

The pressing member 50 presses the cartridge 60 and moves between a first position in which the inspection of the fluidic sample is performed and a second position which is spaced apart from the cartridge 60. The driving unit 40 allows the pressing member 50 to move between the first and second positions.

The driving unit 40 may include a motor 45 providing power to move the pressing member 50, and a lever 43 of which one side is coupled to the pressing member 50 and the other side is coupled to the motor 45. The driving unit 40 may further include a shaft 42 fixing the lever 43. The motor 45 and the lever 43 are coupled with each other through a motor shaft 41. The lever 43 is moved upward and downward with respect to the motor shaft 41 by driving of the motor 45. More specifically, if a rear side of a portion of the lever 43 coupled to the motor shaft 41 is moved upward, an upper side of the portion thereof coupled to the motor shaft 41 is moved downward. Further, if the rear side of the portion coupled to the motor shaft 41 is moved downward, a lower side of the portion coupled to the motor shaft 41 is moved upward. Movement of the lever 43 will be described later.

A protrusion 43a is extended from one side of the driving unit 40 so that the sensing unit 70 may sense a position of the driving unit 40. More specifically, the protrusion 43a is provided to be extended from one side of the lever 43. The protrusion 43a may be extended toward the sensing unit 70. Therefore, the lever 43 is moved by the driving of the motor 45, and the sensing unit 70 senses the position of the driving unit 40 by movement of the protrusion 43a. According to one embodiment of the present invention, since the sensing unit 70 is located at a lower side of the lever 43, the protrusion 43a may be extended to a lower side.

A holder 44 fixing the pressing member 50 is provided at the other side of the lever 43. The pressing member 50 is coupled to the holder 44 and moved up and down by the movement of the lever 43 so as to press the cartridge 60.

According to one embodiment of the present invention, the sensing unit 70 may be a proximity sensor which senses the position of the driving unit 40 by sensing whether the protrusion 43a comes close to the sensing unit 70. More specifically, the sensing unit 70 may be an optical sensor including a light emitting part 71 and a light receiving part 72 receiving light emitted from the light emitting part 71. The emitted light may be infrared light. Further, light emitting diodes (LED) may be used for the light emitting part 71 and the light receiving part 72. The light emitting part 71 and the light receiving part 72 may be provided to protrude with respect to a base part 73. Furthermore, the light emitting part 71 and the light receiving part 72 may be provided to be opposite to each other. Therefore, it is possible to sense whether the protrusion 43a is located between the light emitting part 71 and the light receiving part 72.

However, the sensing unit 70 is not limited thereto. The sensing unit 70 may be a weight sensor which senses the position of the driving unit 40 according to whether the protrusion 43a is in contact with the sensing unit 70.

The driving unit 40 and the sensing unit 70 may be coupled to a frame 30. Also, the installing member 32 in which the cartridge 60 is inserted may be coupled to a front surface of the frame 30. The installing member 32 has an insertion groove 32a in which the cartridge 60 is inserted.

The frame 30 may include an upper plate 30a and a supporting plate 30b supporting the upper plate 30a. The installing member 32 may be coupled to a lower surface of the supporting plate 30b. Further, the motor 45 may be disposed at a lower side of the supporting plate 30b, and the lever 43 may be coupled to an upper portion of the upper plate 30a through the motor shaft 41.

A rear panel 31 is coupled to a rear surface of the frame 30 so as to fix the driving unit 40 in the housing 10. A coupling protrusion 31a coupling the rear panel 31 and the frame 30 may be provided at a surface of the rear panel 31 opposite to the frame 30. A separate coupling member (not shown) may be inserted onto the coupling protrusion 31a so as to couple the rear panel 31 and the frame 30. Also, a supporting rib 31b may be provided on a rear surface of the rear panel 31, and a frame receiving portion 31c in which the frame 30 is inserted may be provided at the rear panel 31.

The cartridge 60 is inserted into the insertion groove 32a of the installing member 32. The cartridge 60 may have a gripping portion 61 grasped by a user. The gripping portion 61 has a streamlined protrusion shape so that the user may stably grasp the cartridge 60.

Also, a fluid receiving portion 62 receiving a fluidic sample may be provided at the cartridge 60. A fluid to be inspected by the test apparatus 1 of the fluidic sample is supplied to the fluid receiving portion 62, and the object fluid may include a bio-sample such as body fluid including blood, tissue fluid, and lymph fluid, saliva, urine, and an environmental sample for water quality management and soil management, but not limited thereto. A user may drop the fluidic sample into the fluid receiving portion 62 using a tool such as a pipette and a spuit. The fluid may flow through a receiving hole formed in the fluid receiving portion 62.

The cartridge 60 is configured such that the inspection part 63 is coupled or welled thereto. The fluid injected through the fluid receiving portion 62 is introduced to the inspection part 63 and reacts with a reagent, thereby performing the inspection. The inspection part 63 includes an inspection chamber 63a in which the fluid and the reagent are received.

The pressing member 50 may include a head portion 51 coupled with the driving unit 40, and a body portion 52 pressing the cartridge 60. The head portion 51 may be coupled to the holder 44 of the lever 43. Description of the pressing member 50 will be described below.

Figure 6:
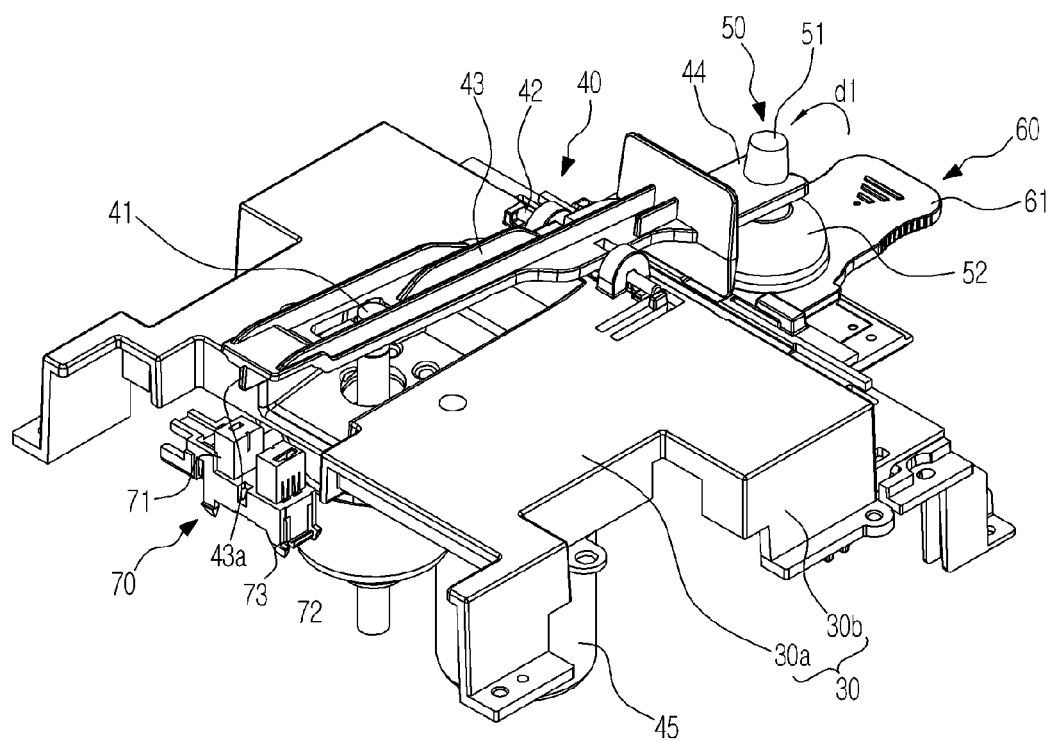
FIG. 6 is a view schematically illustrating a state in which a pressing member of a test apparatus of a fluidic sample is located at a first position in accordance with one embodiment of the present invention.
Figure 7:
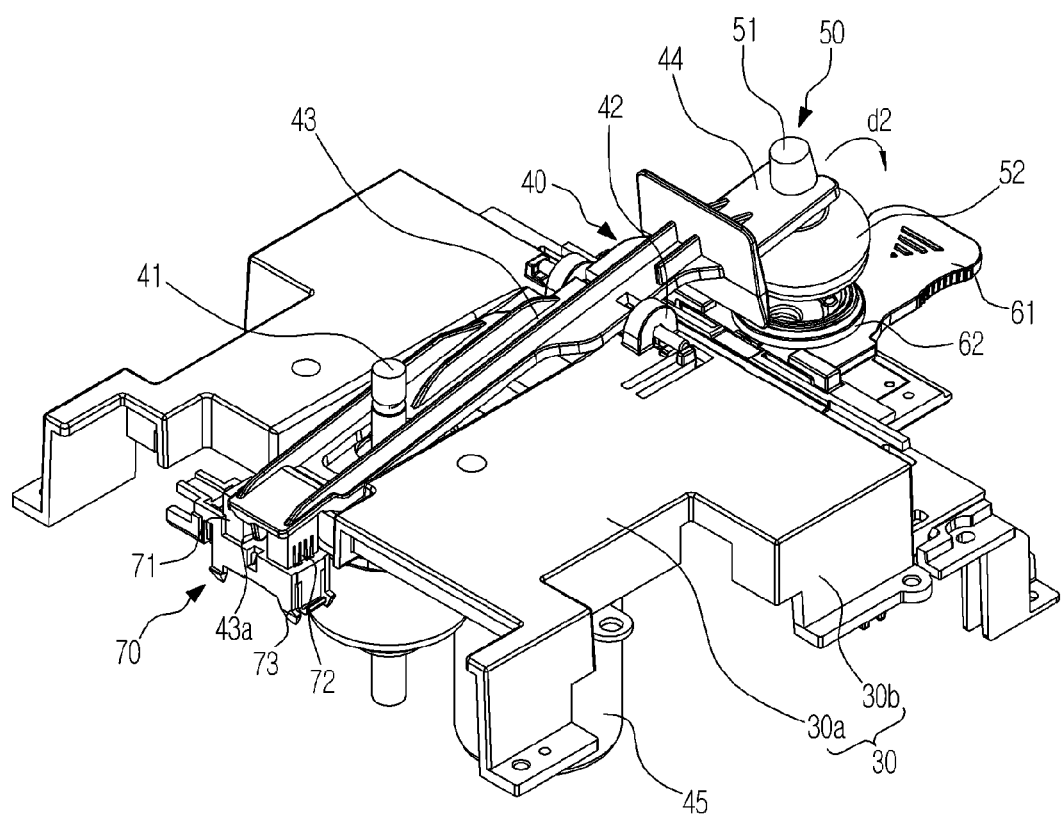
FIG. 7 is a view schematically illustrating a state in which a pressing member of a test apparatus of a fluidic sample is located at a second position in accordance with one embodiment of the present invention.

FIG. 6 is a view schematically illustrating a state in which the pressing member of a test apparatus of a fluidic sample is located at the first position in accordance with one embodiment of the present invention, and FIG. 7 is a view schematically illustrating a state in which the pressing member of a test apparatus of a fluidic sample is located at the second position in accordance with one embodiment of the present invention.

As illustrated in FIGS. 6 and 7, the pressing member 50 is moved between the first and second positions by the driving of the motor 45. The pressing member 50 presses the cartridge 60 at the first position, and is spaced apart from the cartridge 60 at the second position.

At the first position, a front surface of the lever 43 coupled with the pressing member 50 is moved downward, and a rear surface thereof in which the protrusion 43a is located is moved upward. Therefore, the sensing unit 70 does not sense the position of the protrusion 43a.

At the second position, the front surface of the lever 43 coupled with the pressing member 50 is moved upward, and the rear surface thereof in which the protrusion 43a is located is moved downward. Therefore, the sensing unit 70 senses the position of the protrusion 43a. In one embodiment of the present invention, if the test apparatus 1 of the fluidic sample is turned on, the pressing member 50 is spaced apart from the cartridge 60, and thus the protrusion 43a may be moved toward the sensing unit 70. Therefore, the sensing unit 70 may recognize a starting point of the driving unit 40 before starting the inspection of the fluid.

The pressing member 50 can move from the first position to the second position in a direction d1, and also can move from the second position to the first position in a direction d2.

Figure 8:
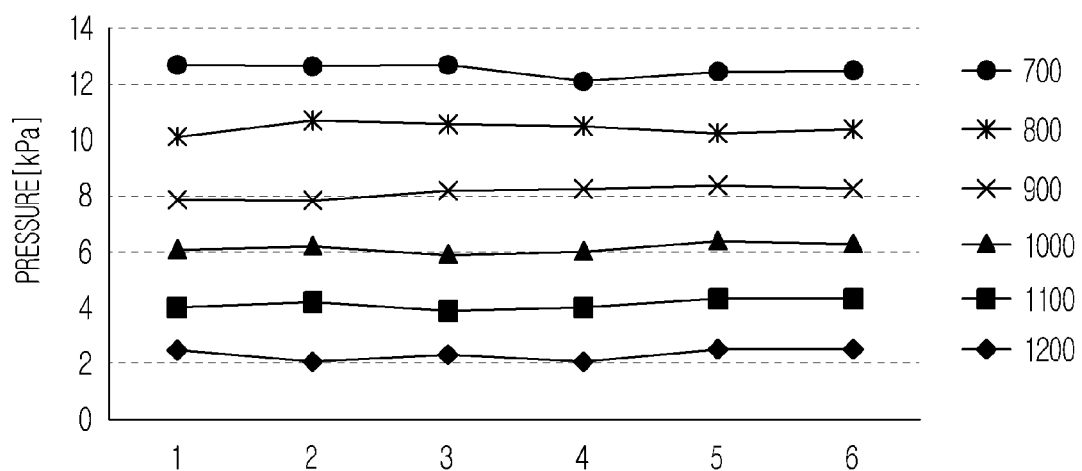
FIG. 8 is a graph illustrating pressure applied to a cartridge per transfer distance of a motor in a test apparatus of a fluidic sample in accordance with one embodiment of the present invention.

FIG. 8 is a graph illustrating pressure applied to the cartridge per transfer distance of the motor in a test apparatus of a fluidic sample in accordance with one embodiment of the present invention.

As illustrated in FIG. 8, the pressure applied to the cartridge 60 by the pressing member 50 depends on a transfer distance of the motor. That is, it is understood from FIG. 8 that, if the transfer of the motor 45 is the same, the pressure applied to the cartridge 60 by the pressing member 50 is also maintained consistently.

The contents in FIG. 8 may be tabulated as follows:

TABLE 1

| Transfer distance of motor (n μm) | The number of tests | | | | | | Average (kPa) |
| --- | --- | --- | --- | --- | --- | --- | --- |
| | 1 | 2 | 3 | 4 | 5 | 6 | |
| 700 | 2.5 | 2.1 | 2.3 | 2.1 | 2.5 | 2.5 | 2.3 |
| 800 | 4 | 4.2 | 3.9 | 4 | 4.3 | 4.3 | 4.1 |
| 900 | 6.1 | 6.2 | 5.9 | 6 | 6.4 | 6.3 | 6.2 |
| 1000 | 7.9 | 7.8 | 8.2 | 8.3 | 8.4 | 8.3 | 8.2 |
| 1100 | 10.1 | 10.7 | 10.6 | 10.5 | 10.2 | 10.4 | 10.4 |
| 1200 | 12.7 | 12.6 | 12.7 | 12.1 | 12.4 | 12.5 | 12.5 |

As illustrated in Table 1, if the transfer of the motor is the same, the pressure applied to the cartridge is also maintained consistently. In one embodiment of the present invention, the position of the driving unit 40 is sensed by the sensing unit 70, and thus the transfer distance of the motor 45 may also be sensed. Therefore, it is possible to control the test apparatus 1 of the fluidic sample so that the uniform pressure is applied to the cartridge 60. Such a control of the test apparatus 1 of the fluidic sample can be performed by a control part (not shown).

Figure 9:
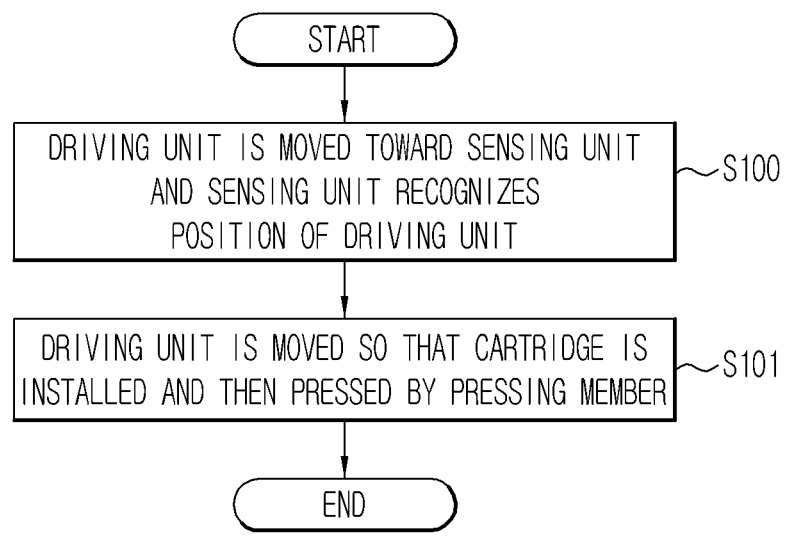
FIG. 9 is a flowchart schematically illustrating a control method of a test apparatus of a fluidic sample in accordance with one embodiment of the present invention.
Figure 10:
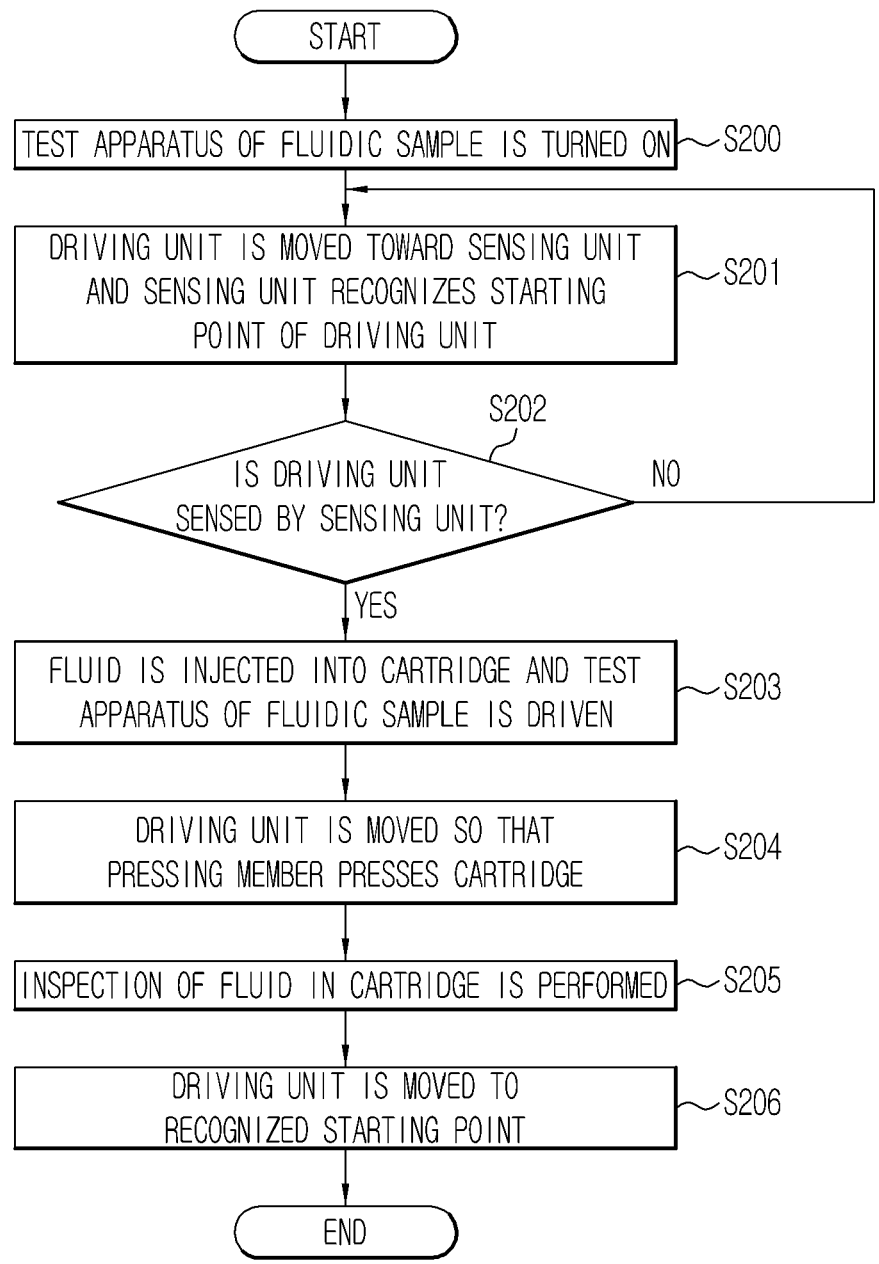
FIG. 10 is a flowchart illustrating a control method of a test apparatus of a fluidic sample in accordance with one embodiment of the present invention.

FIG. 9 is a flowchart schematically illustrating a control method of a test apparatus of a fluidic sample in accordance with one embodiment of the present invention, and FIG. 10 is a flowchart illustrating a control method of a test apparatus of a fluidic sample in accordance with one embodiment of the present invention.

As illustrated in FIGS. 9 and 10, according to one embodiment of the present invention, the driving unit 40 is moved toward the sensing unit 70, and the sensing unit 70 recognizes the position of the driving unit 40 (S100). The driving unit 40 is moved so that the cartridge 60 is installed and then pressed by the pressing member 50 (S101). The sensing unit 70 recognizes the position of the driving unit 40, determines the starting point of the driving unit 40, and measures the transfer distance of the motor 45, and thus it is possible to control the pressure applied to the pressing member 50. Therefore, since the uniform pressure may be applied when performing the inspections of various kinds of fluids, it is possible to prevent occurrence of errors in the inspections.

Hereinafter, a control method of a test apparatus 1 of a fluidic sample in accordance with one embodiment of the present invention will be described in detail with reference to FIG. 10.

As illustrated in FIG. 10, when the test apparatus 1 of the fluidic sample is turned on (S200), the driving unit 40 is moved toward the sensing unit 70, and the sensing unit 70 recognizes the starting point of the driving unit 40 (S201). Here, the starting point means a state in which the pressing member 50 is located to be spaced apart from the cartridge 60.

The sensing unit 70 determines whether the driving unit 40 is sensed (S202). If the driving unit 40 is not sensed, it means that the driving unit 40 is not located at the starting point, and thus the step S201 of moving the driving unit 40 toward the sensing unit 70 is performed again.

If the driving unit 40 is sensed by the sensing unit 70, it means that the driving unit 40 is located at the starting point, and thus a fluid is injected into the cartridge 60 and then the test apparatus 1 of the fluidic sample is driven (S203).

The driving unit 40 moves the pressing member 50 so that the cartridge 60 may be pressed by the pressing member 50 (S204). Since the control part (not shown) already knows the starting point, the control part (not shown) may control the pressing member 50 to apply a predetermined pressure to the cartridge 60.

The fluid in the cartridge 60 is moved to the inspection part 63 by the pressure of the pressing member 50 and then inspected (S205).

After the inspection is completed, the driving unit 40 may move the pressing member 50 back to the recognized starting point (S206).

According to one embodiment of the present invention as described above, since the control part (not shown) controls the movement of the driving unit 40 so that the uniform pressure is applied to the cartridge 60, it is possible to prevent the fluid from leaking from the cartridge 60 and also allow the fluid to be smoothly moved to the inspection part 63. Further, since the sensing unit 70 senses the position of the driving unit 40 so that the inspection is started after the driving unit 40 is located at the starting point, it is possible to perform a precise inspection.

Figure 11:
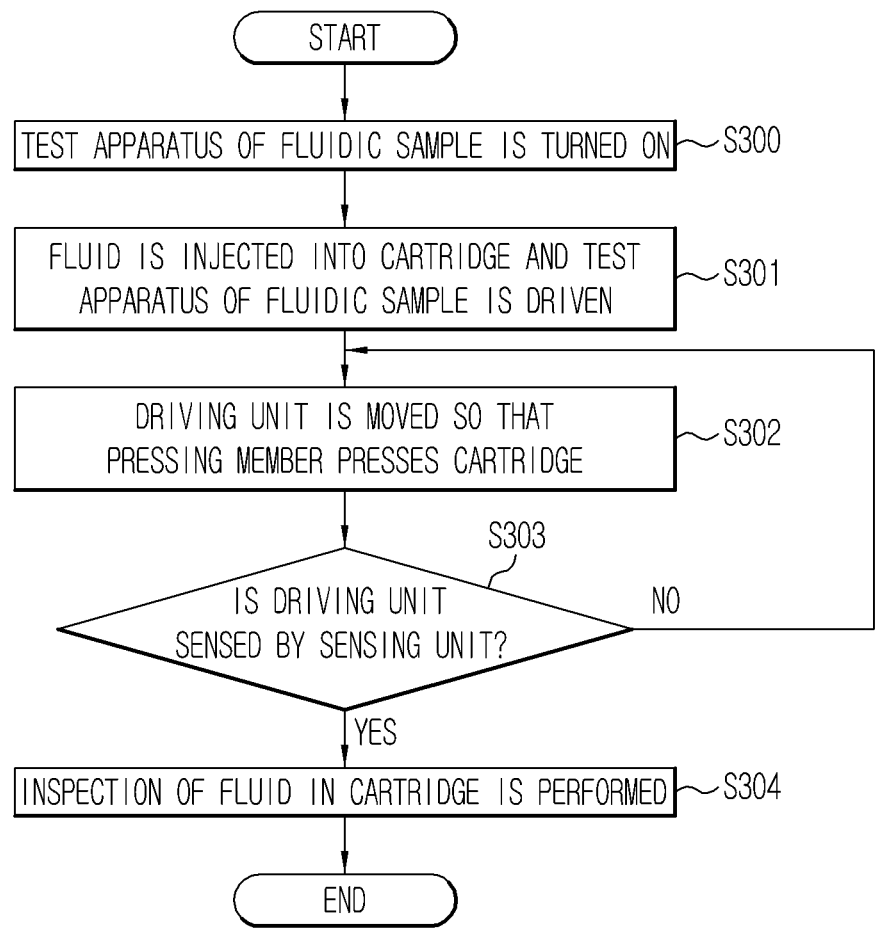
FIG. 11 is a flowchart illustrating a control method of a test apparatus of a fluidic sample in accordance with another embodiment of the present invention.

FIG. 11 is a flowchart illustrating a control method of a test apparatus of a fluidic sample in accordance with another embodiment of the present invention.

As illustrated in FIG. 11, in one embodiment of the present invention, if the test apparatus 1 of the fluidic sample is turned on (S300), a fluid is injected into the cartridge 60 and then the test apparatus 1 of the fluidic sample is driven (S301).

After that, the driving unit 40 is moved so that the cartridge 60 is pressed by the pressing member 50 (S302). The control part (not shown) determines whether the driving unit 40 is sensed by the sensing unit 70 (S303). If the driving unit 40 is not sensed, the control part (not shown) moves the driving unit 40 so that the cartridge 60 is pressed by the pressing member 50 (S302). If the driving unit 40 is sensed by the sensing unit 70, the fluid in the cartridge 60 is inspected (S304).

According to one embodiment of the present invention illustrated in FIG. 11, if the driving unit 40 is sensed by the sensing unit 70, it means that the pressing member 50 is located at the first position. Therefore, the control part (not shown) may determine whether the inspection may be started.

Figure 12:
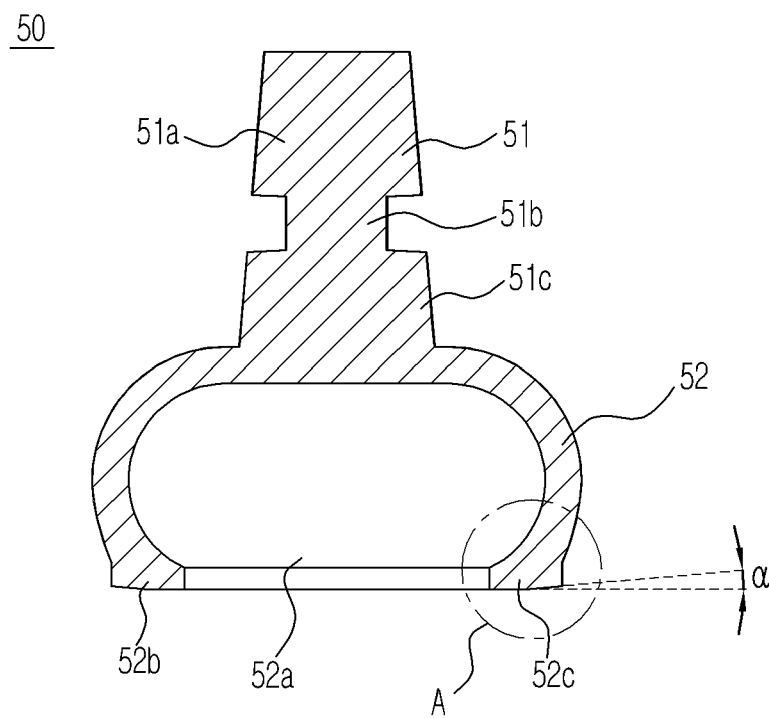
FIG. 12 is a view illustrating a pressing member of a test apparatus of a fluidic sample in accordance with one embodiment of the present invention.

FIG. 12 is a view illustrating a pressing member of a test apparatus of a fluidic sample in accordance with one embodiment of the present invention.

As illustrated in FIG. 12, the pressing member 50 may include the head portion 51 coupled with the holder 44 of the driving unit 40, and the body portion 52 pressing the cartridge 60.

The pressing member 50 is made of a flexible material. For example, the pressing member 50 may be made of silicon, urethane, and rubber, but not limited thereto and may also be made of various deformable materials.

The head portion 51 may include a first head portion 51a located at an upper side, and a second head portion 51c located at a lower side. A neck portion 51b may be provided between the first and second head portions 51a and 51c so as to be concave inside. The neck portion 51b is fitted to the holder 44 so that the pressing member 50 is coupled to the driving unit 40.

A contacting surface 52b which comes in contact with the cartridge 60 to press it may be provided at a lower surface of the body portion 52. Further, a deformable portion 52a may be provided at a center of the body portion 52 so that the pressing member 50 may be flexibly deformed when the pressure is applied. According to one embodiment of the present invention, the deformable portion 52a may be provided so that an inside of the body portion 52 is empty.

The contacting surface 52b may include an inclined portion 52c which is at least partially inclined on the contacting surface 52b. According to one embodiment of the present invention, the inclined portion 52c may be provided at an edge of the contacting surface 52b. According to one embodiment of the present invention, the inclined portion 52c may be provided to be upwardly inclined toward an outside of the body portion 52. Also, the inclined portion 52c may have an angle α of 2 to 8° with respect to a horizontal plane, but not limited thereto.

The inclined portion 52c serves to deform a shape of the contacting surface 52b and define a space when the pressing member 50 is in contact with the cartridge 60, whereby the pressure applied by the pressing member 50 is prevented from being changed. Therefore, the contacting surface 52b is prevented from being deformed in an undesirable direction, and thus the uniform pressure may be applied to the entire areas of the cartridge 60. Therefore, it is possible to reduce errors in the inspection results due to a pressure difference applied by the pressing member 50.

Figure 13:
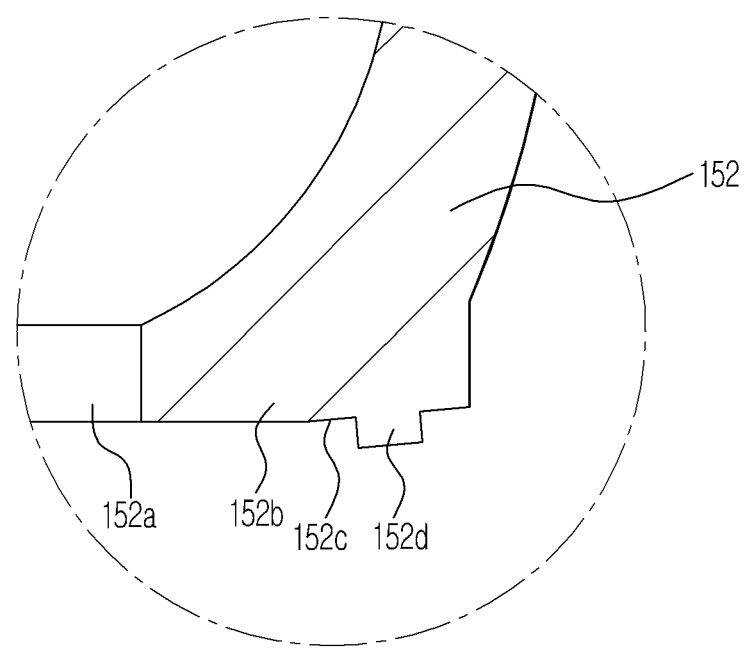
FIG. 13 is an enlarged view illustrating a pressing member of a test apparatus of a fluidic sample in accordance with another embodiment of the present invention.
Figure 14:
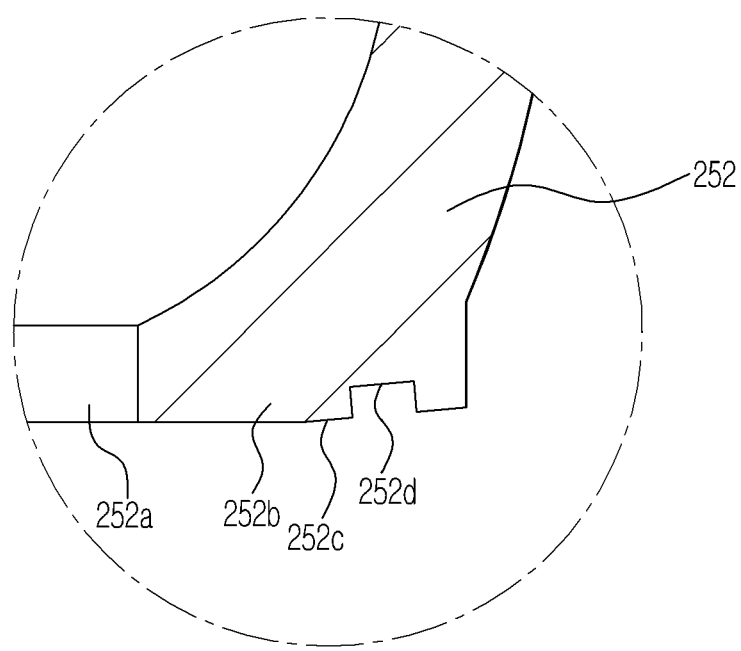
FIG. 14 is an enlarged view illustrating a pressing member of a test apparatus of a fluidic sample in accordance with yet another embodiment of the present invention.

FIG. 13 is an enlarged view illustrating a pressing member of a test apparatus of a fluidic sample in accordance with another embodiment of the present invention, and FIG. 14 is an enlarged view illustrating a pressing member of a test apparatus of a fluidic sample in accordance with yet another embodiment of the present invention.

FIGS. 13 and 14 are relevant to an A portion of FIG. 12.

According to one embodiment of the present invention illustrated in FIG. 13, at least a part of a contacting surface 152b of a body portion 152 may protrude, thereby defining at least one protruding portion 152d. According to one embodiment of the present invention, the protruding portion 152d is provided on an inclined portion 152c. However, if the protruding portion 152d is provided, it may not be necessary to provide the inclined portion 152c.

According to one embodiment of the present invention illustrated in FIG. 14, at least a part of a contacting surface 252b of a body portion 252 may be concave, thereby defining a concave portion 252d. According to one embodiment of the present invention, the concave portion 252d is provided on an inclined portion 252c. However, if the concave portion 252d is provided, it may not be necessary to provide the inclined portion 252c.

The protruding portion 152d and the concave portion 252d prevent the pressing member from being deformed when the pressing member comes in contact with the cartridge, whereby the pressure applied by the pressing member is prevented from being changed.

In the test apparatus of the fluidic sample according to one aspect of the present invention, since the sensing unit can recognize the position of the driving unit, the pressing member can apply the uniform pressure to the cartridge, thereby reducing the errors in the inspection.

In the test apparatus of the fluidic sample according to another aspect of the present invention, it is possible to prevent the pressure applied to the cartridge from being changed time after time due to the deformation of the pressing member.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A test apparatus of a fluidic sample, comprising:
   a housing;
   an installing member in which a cartridge receiving a fluid is inserted;
   a pressing member which is disposed in the housing to press the cartridge and perform an inspection of the fluid;
   a driving unit of which at least a part is coupled to the pressing member so as to movably drive the pressing member; and
   a sensing unit of which at least a part is opposite to the driving unit so as to sense a position of the driving unit and to determine a starting point of the driving unit,
   wherein the driving unit comprises a motor providing power to move the pressing member,
   wherein the pressing member applies substantially uniform pressure to the cartridge by measuring a transfer distance of the motor.

2. The test apparatus according to claim 1, wherein a protrusion is extended from one side of the driving unit so that the sensing unit senses the position of the driving unit.

3. The test apparatus according to claim 2, wherein the sensing unit is a proximity sensor which senses the position of the driving unit by sensing whether the protrusion comes close to the sensing unit.

4. The test apparatus according to claim 3, wherein the proximity sensor is an optical sensor comprising a light emitting part emitting light and a light receiving part receiving the light emitted from the light emitting part, and
   the optical sensor senses the position of the driving unit by sensing whether the protrusion is located between the light emitting part and the light receiving part.

5. The test apparatus according to claim 2, wherein the sensing unit is a weight sensor which senses the position of the driving unit according to whether the protrusion is in contact with the sensing unit.

6. The test apparatus according to claim 2, wherein a lever transmits the power of the motor to the pressing member, and the protrusion is extended from the lever toward the sensing unit.

7. The test apparatus according to claim 6, wherein the sensing unit is located at a lower side of the lever.

8. The test apparatus according to claim 1, wherein the pressing member comprises a head portion coupled with the driving unit, and a body portion pressing the cartridge.

9. The test apparatus according to claim 8, wherein a contacting surface of the body portion, which is in contact with the cartridge, comprises an inclined portion which is at least partially inclined on the contacting surface.

10. The test apparatus according to claim 9, wherein the inclined portion is provided to be upwardly inclined toward an outside of the body portion.

11. The test apparatus according to claim 8, wherein a contacting surface of the body portion, which is in contact with the cartridge, comprises at least one protruding portion which at least partially protrudes from the contacting surface.

12. The test apparatus according to claim 8, wherein a contacting surface of the body portion, which is in contact with the cartridge, comprises at least one concave portion which is at least partially concave in the contacting surface.

13. The test apparatus according to claim 1, further comprising a frame of which one side is coupled with the driving unit, and the other side is coupled with the installing member.

14. The test apparatus according to claim 1, further comprising a control part which senses a movement degree of the driving unit and controls the driving unit to uniformly move the pressing member.

15. A test apparatus of a fluidic sample, comprising:
a housing;
a frame which is disposed in the housing;
a pressing member coupled to one side of the frame and moving between a first position which presses a cartridge receiving a fluid and performs an inspection of the fluid and a second position which is spaced apart from the cartridge;
a driving unit which is coupled to the other side of the frame so as to move the pressing member between the first and second positions; and
a sensing unit which recognizes movement of the driving unit and determines whether the pressing member is located at the first position or the second position,
wherein the driving unit comprises a motor providing power to move the pressing member,
wherein the pressing member applies substantially uniform pressure to the cartridge by measuring a transfer distance between the first position and the second position of the motor.

16. The test apparatus according to claim 15, wherein the sensing unit is a proximity sensor which senses the position of the driving unit by sensing whether at least a part of the driving unit comes close to the sensing unit.

17. The test apparatus according to claim 15, wherein the sensing unit is a weight sensor which senses the position of the driving unit according to whether at least a part of the driving unit is in contact with the sensing unit.

18. The test apparatus according to claim 15, wherein the driving unit further comprises:
a lever transmitting the power of the motor to the pressing member; and
a protrusion extended from the driving unit toward the sensing unit so as to be moved toward the sensing unit.

19. A control method of a test apparatus of a fluidic sample including a pressing member which presses a cartridge receiving a fluid, a driving unit which movably drives the pressing member, and a sensing unit which senses a position of the driving unit, the control method comprising:
moving at least a part of the driving unit, and recognizing a position of the driving unit by the sensing unit; and
installing the cartridge, and moving the driving unit to move the pressing member so as to press the cartridge,
wherein the recognizing of the position of the driving unit includes recognizing a starting point of the driving unit,
wherein the pressing member applies substantially uniform pressure to the cartridge by measuring a transfer distance of the motor.

20. The control method according to claim 19, further comprising moving the driving unit to the recognized starting point after an analysis of the fluid in the cartridge is performed.

21. The control method according to claim 19, wherein the test apparatus of the fluidic sample further includes a control part which controls a movement degree of the driving unit, and
the control part recognizes a position of the driving unit sensed by the sensing unit as a starting point of the driving unit, senses the movement degree of the driving unit, and controls the pressing member to apply uniform pressure to the cartridge.

22. The control method according to claim 21, wherein the control part performs an inspection when the driving unit is sensed by the sensing unit, and moves the driving unit to the starting point when the driving unit is not sensed by the sensing unit.

23. The control method according to claim 19, wherein the recognizing of a position of the driving unit recognizes one point at which the driving unit moves the pressing member so as to press the cartridge.

* * * * *